(12) United States Patent
Zhang et al.

(10) Patent No.: US 9,339,553 B2
(45) Date of Patent: May 17, 2016

(54) LIQUID COMPOSITIONS OF INSOLUBLE DRUGS AND PREPARATION METHODS THEREOF

(75) Inventors: Qiang Zhang, Beijing (CN); Wenbing Dai, Beijing (CN); Jiancheng Wang, Beijing (CN); Xuan Zhang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 109 days.

(21) Appl. No.: 13/819,407

(22) PCT Filed: Aug. 31, 2011

(86) PCT No.: PCT/CN2011/079194
§ 371 (c)(1),
(2), (4) Date: Feb. 27, 2013

(87) PCT Pub. No.: WO2012/028101
PCT Pub. Date: Mar. 8, 2012

(65) Prior Publication Data
US 2013/0156853 A1    Jun. 20, 2013

(30) Foreign Application Priority Data
Sep. 1, 2010 (CN) .......................... 2010 1 0268940

(51) Int. Cl.
A61K 47/44    (2006.01)
A61K 9/00     (2006.01)
A61K 9/107    (2006.01)
A61K 47/24    (2006.01)
A61K 9/08     (2006.01)

(52) U.S. Cl.
CPC ............... *A61K 47/44* (2013.01); *A61K 9/0019* (2013.01); *A61K 9/08* (2013.01); *A61K 9/107* (2013.01); *A61K 47/24* (2013.01)

(58) Field of Classification Search
CPC ....... A61K 9/0019; A61K 9/107; A61K 9/08; A61K 47/44; A61K 47/24
See application file for complete search history.

(56) References Cited

U.S. PATENT DOCUMENTS

| 6,348,491 | B1 * | 2/2002  | Chu et al. ................ 514/449 |
| 8,075,917 | B2   | 12/2011 | Chung et al. |
| 8,557,861 | B2   | 10/2013 | Chen |
| 2004/0092428 | A1 | 5/2004 | Chen et al. |
| 2004/0115255 | A1 | 6/2004 | Leigh et al. |
| 2005/0026898 | A1 | 2/2005 | Peracchia et al. |
| 2006/0134145 | A1 | 6/2006 | Matsuda et al. |
| 2006/0210622 | A1 | 9/2006 | Pace et al. |
| 2007/0077286 | A1 | 4/2007 | Ishihara et al. |
| 2007/0207173 | A1 | 9/2007 | Chen |
| 2008/0145411 | A1 | 6/2008 | Shinagawa et al. |

FOREIGN PATENT DOCUMENTS

| CN | 1562014 A | 1/2005 |
| CN | 1634058 A | 7/2005 |
| CN | 101019832 A | 8/2007 |
| CN | 101204373 | * 6/2008 |
| CN | 101926757 A | 12/2010 |
| EP | 2 491 919 A1 | 8/2012 |
| JP | 3-176425 A | 7/1991 |
| JP | 2012-051823 A | 3/2012 |
| WO | 88/06438 A1 | 9/1988 |
| WO | 92/05771 A1 | 4/1992 |
| WO | 99/22703 A1 | 5/1999 |
| WO | 2008/042841 A2 | 4/2008 |
| WO | 2009/011861 A1 | 1/2009 |
| WO | 2011/113301 A1 | 9/2011 |

OTHER PUBLICATIONS

English Language Machine Translation of Shihai et al., CN 101204373, Paclitaxel lipid microsphere injection and its preparation method, assessed on Jul. 7, 2013.*
PCT Search Report for PCT Application No. PCT/CN2011/079194 mailed Dec. 8, 2011.
Supplementary European Search Report for EP Application No. 11821127.5 mailed Jul. 3, 2015.

* cited by examiner

*Primary Examiner* — Johann R Richter
*Assistant Examiner* — Genevieve S Alley
(74) *Attorney, Agent, or Firm* — Sutherland Asbill & Brennan LLP

(57) ABSTRACT

A liquid composition of an insoluble medicament and a preparation method thereof are disclosed. The composition includes insoluble medicament, oil for injection, phospholipid, and solvent; the percentage by weight of each component is as follows: insoluble medicament 0.01-10%, oil for injection 0%-20%, phospholipid 10-80%, solvent 20-89%. The preparation method for the composition includes the following steps: dissolving an insoluble medicament into solvent or oil for injection or a mixture thereof firstly, and then adding other components, and mixing uniformly; or dissolving an insoluble medicament into a mixture of other components, and mixing uniformly; or dissolving an insoluble medicament into part of solvent firstly, and then adding into a mixed solvent of other components and the remaining solvent, and mixing uniformly.

30 Claims, 3 Drawing Sheets

LIQUID COMPOSITIONS OF INSOLUBLE DRUGS AND PREPARATION METHODS THEREOF

CROSS REFERENCE TO RELATED APPLICATIONS

This application claims the priority benefit of PCT/CN2011/079194 filed on Aug. 31, 2011 and Chinese Application No. 201010268940.0 filed on Sep. 1, 2010. The contents of these applications are hereby incorporated by reference in their entirety.

TECHNICAL FIELD

The invention belongs to the pharmaceutical formulation field, and relates to the technology for improving the solubility of an water-insoluble medicament, particularly to a liquid composition of an water-insoluble medicament and a preparation method thereof.

BACKGROUND OF THE RELATED ART

Statistically, in the development of new medicaments, the developments for about 40% of medicaments are limited due to the water solubility problem, and some of the medicaments are even insoluble in some common organic solvents. The solubilization of water insoluble medicaments is one of important issues in pharmacy research. Common solubilization methods include modulation of pH value, use of latent solvent, cosolvent, cyclodextrin clathrate, phospholipid complex, surfactant solubilization, preparation of micelles, liposomes, microspheres, solid lipid nanoparticles, microemulsions, and fat emulsions and the like; or chemical methods of introducing water-soluble groups by utilizing suitable groups in the structure of the medicament to obtain derivates with greater water solubility.

Some medicament molecules are dissociable weak acids or weak bases. Dissociation of insoluble medicaments by adjusting the pH value of the solution is a simple and effective method for solubility improvement. In injection administration, buffer pair capacity issue should be noted. Insoluble medicaments tend to be supersaturated due to the dilution by blood, since the blood possesses good buffer ability.

For some nonpolar medicaments, the mixture of less polar organic solvents (latent solvents) with water is generally used to dissolve the medicaments. 10% of injections approved by FDA use latent solvents. This kind of formula could not only improve the solubility of some medicaments significantly, but also reduce the hydrolysis reaction of some medicaments in the solutions, thus improving the stability of the formulations. However, for some insoluble medicaments, a higher fraction of organic solvents is required for achieving the requirement of solubility. For example, phenobarbital injection requires 10% ethanol and 67.8% propylene glycol for dissolving. However, high fraction of organic solvents tends to induce local irritation of injection site and phlebitis. For example, if the formula contains more than 10% ethanol, significant pain of injection will occur.

Cyclodextrin clathration can be used to a variety of medicaments, the unique cage structure of which could form host and guest molecule complex, wherein nonpolar medicament molecules are located inside the nonpolar cage structure, and polyhydroxy outside the cyclodextrin possesses high affinity with polar water molecule, thus improving solubility. However, for some insoluble medicaments, the drug loading capacity is on the low side. The solubilization effect of medicaments in cyclodextrin depends on the binding constant of medicament molecule with cyclodextrin. For example, the binding constant of benzodiazepine medicaments is relatively low, therefore after comparison, the traditional latent solvent formula has been selected. In other words, not all medicaments could utilize cyclodextrin clathration. Furthermore, the categories of cyclodextrins are limited, and the cyclodextrins possess significant toxicity and thus not many have been used in injections currently.

In recent years, liposomes, microspheres, solid lipid nanoparticles, microemulsions, and hydrophilic derivates are used to improve the water solubility of insoluble medicaments. There are many researches and patents both at home and abroad. Although these researches have obtained some progress, there still exist problems such as the instable effect, complexity of formulation and process, low drug loading capacity, high toxicity of surfactants as well as high costs of development, and the like.

Surfactants improve the solubility of nonpolar medicaments in water by forming micelle. When used by clinical injection, many insoluble anti-tumor medicaments have to utilize surfactants for solubilization. Currently, injectable surfactants approved both at home and abroad include polysorbate (mainly POLYSORBATE 80, i.e. Tween 80), poloxamer (mainly POLOXAMER 188), Cremophor EL (mainly CREMOPHOR EL), and phospholipid. Wherein, poloxamer 188 and phospholipid have strong emulsifying ability, but are weak in solubilization, and mainly used in intravenously injectable fat emulsion. Cremophor EL and Tween 80 have relatively strong solubilization and emulsifying abilities, could solubilize insoluble medicaments into non-aqueous medium, and could form aqueous solution or emulsion by formulating with water for injection (or injectable normal saline solution, injectable dextrose solution) before use. In this kind of ready-to-use injections, the solubilization and emulsifying abilities of Cremophor EL or Tween 80 both play important roles.

For example, commercial paclitaxel, teniposide injections include a large amount of Cremophor EL, and could be formulated into an aqueous solution with aqueous medium such as water for injection before use; docetaxel injection includes a large amount of Tween 80, and could be formulated into an aqueous solution with aqueous medium such as water for injection before use; there are also many other related patent reports in which Cremophor EL or Tween 80 is selected. In Patent CN200610037337.3, phospholipid, other surfactants (Tween 80, poloxamer 188, and Cremophor EL) and non-aqueous solvents are used to prepare injections for insoluble medicament paclitaxel; Chinese Patent 200710198956.7 relates to injectable teniposide injections, which formula contains Tween 80 as surfactant. Generally, it is difficult to formulate insoluble medicament injections without Cremophor EL or Tween 80.

However, for injections, which contain Cremophor EL or Tween 80, some patients will have adverse reactions such as dermatitis medicamentosa, tachypnea, bronchospasm, hypotension, and haemolysis after administration, which results in much inconvenience for clinical use, and causes significant pain for the patients, so the compliance for medication is poor. In recent years, many researchers in the pharmacy field at home and abroad focus on the studies on new anti-tumor delivery systems for reducing or replacing Cremophor EL or Tween 80. Since these two surfactants could induce extremely severe side effects, they are limitedly used in injections. Obviously, injections without these two surfactants are more preferable for improving the compliance for medication.

Contents of the Invention

Based on the above background, we made a series of researches, and surprisingly found that in suitable conditions, insoluble medicaments could also be formulated into clear solution (true solution) without surfactant Cremophor EL or Tween 80, and once this solution was hydrated with injectable solvents (such as 5% dextrose solution, normal saline, water for injection), it will be stable within 8 hours, which is in conformity with the requirement for clinical medication. Thus, we designed a liquid composition of an insoluble medicament without surfactant Cremophor EL or Tween 80.

Therefore, the first aim of this invention is to provide a liquid composition of an insoluble medicament. In this liquid composition of an insoluble medicament, safe and intravenously injectable pharmaceutic adjuvant phospholipid and oil for injection as well as solvent such as absolute ethanol are used without any surfactant which could induce significant side effects. Such a liquid composition could eliminate the hidden danger of significant side effects caused by Cremophor EL or Tween 80 in commercially available formulations, thereby significantly improving the compliance of patients. Such a liquid composition of an insoluble medicament is a true solution, has good stability, and could form emulsion for intravenous injection after being dispersed with an injectable solution. Such a liquid composition of an insoluble medicament is easy to formulate, and is suitable for industrial production, as compared with some currently commercially available formulations.

Specifically, the liquid composition of an insoluble medicament of this invention contains insoluble medicament, oil for injection, phospholipid, solvent, with the following percentage by weight for each component:
insoluble medicament 0.01-10%,
oil for injection 0%-20%,
phospholipid 10-80%,
solvent 20-89%.

Preferably, the components and percentages by weight thereof in the liquid composition of an insoluble medicament of this invention are as follows:
insoluble medicament 0.1-2.5%,
oil for injection 0.5%-10%,
phospholipid 20-45%,
solvent 42.5-79%.

More preferably, the components and percentages by weight thereof in the liquid composition of an insoluble medicament of this invention are as follows:
insoluble medicament 0.1-2.5%,
oil for injection 0.5%-3%,
phospholipid 25-40%,
solvent 55-70%.

With respect to the liquid composition of an insoluble medicament of this invention, said "insoluble medicament" refers to a medicament which is known to be applicable in the pharmaceutical field, and the solubility of which in water is lower with respect to the efficient dosage thereof, and particularly refers to a medicament which is recorded to be "slightly soluble", "very slightly soluble" or "practically undissolved or undissolved" in terms of solubility in "General Notices" of Pharmacopeia of the People's Republic of China. In other words, it refers to a medicament wherein the amount of solvent (the amount of water) required for dissolving 1 g or 1 mL solute is above 100 mL (with the concentration being below 1%), preferably 1000 mL (with the concentration being below 0.1%), and more preferably 10000 mL (with the concentration being below 0.01%).

In the liquid composition of an insoluble medicament of this invention, the insoluble medicament includes, but not limits to: docetaxel, paclitaxel, capecitabine, oxaliplatin, gefitinib, doxorubicin, irinotecan, gemcitabine, pemetrexed, temozolomide, imatinib, vinorelbine, letrozole, teniposide, etoposide, podophyllotoxin, camptothecin, 10-hydroxycamptothecin, 9-hydroxycamptothecin, 7-ethyl-10-hydroxycamptothecin SN-38, topotecan, irinotecan, vinblastine, vincristine, vindesine, vinflunine, vinpocetine, norcantharidin, silibinin, propofol, florfenicol, mitiglinide, artemisinin, dihydroartemisinin, sirolimus, ibuprofen, nitrendipine, nicardipine, nimodipine, gliclazide, cisapride, nifedipine, felodipine, glibenclamide, acyclovir, oleanolic acid, breviscapine, ferulic acid, acetaminophen, clindamycin palmitate, penclomedine, Vitamin A, tamoxifen, navelbine, valproic acid, tacrolimus, ciclosporin A, amphotericin B, ketoconazole, domperidone, sulpiride, fenofibrate, bezafibrate, azithromycin, itraconazole, miconazole, brimoxidine, latanoprost, silibinin, erythromycin, roxithromycin, rifaximin, cisapride, cyclosporin, diclofenac, felodipine, ibuprofen, indomethacin, nicardipine, nifedipine, teldane, theophylline, ketoprofen, furosemide, spironolactone, dipyridamole, piroxicam, mefenamic acid, trichloromethiazide, indolol and the like or a mixture thereof, wherein the insoluble medicament is preferably insoluble anti-tumor medicaments, such as paclitaxel, docetaxel, capecitabine, vinorelbine, temozolomide, doxorubicin, gefitinib, teniposide, etoposide, podophyllotoxin, artemisinin, camptothecin, vinblastine and the like or a mixture thereof. More preferably, the insoluble medicament is paclitaxel, docetaxel, capecitabine, vinorelbine, temozolomide, doxorubicin, gefitinib, teniposide, etoposide, artemisinin, camptothecin or the mixture of paclitaxel and teniposid.

The phospholipids in the liquid composition of an insoluble medicament of this invention include natural phospholipids, semisynthetic phospholipids, synthetic phospholipids or a mixture thereof. One of natural phospholipids or the mixture thereof is preferred. Preferably, the natural phospholipids are lecithin, more preferably egg yolk lecithin, soybean lecithin or a mixture of them in any proportion.

The semisynthetic phospholipids and synthetic phospholipids include, but not limit to hydrogenated soybean phosphatidylcholine (HSPC), dioleoyl phosphatidylcholine (DOPC), dimyristoyl phosphatidylethanolamine (DMPE), dipalmitoyl phosphatidylethanolamine (DPPE), dimyristoyl phosphatidylserine (DMPS), distearyl phosphatidylethanolamine (DSPE), dilauroyl phosphatidylcholine (DLPC), dimyristoyl phosphatidylcholine (DMPC), dipalmitoyl phosphatidylcholine (DPPC), distearyl phosphatidylcholine (DPPC), distearyl phosphatidylcholine (DSPC), 1-myristoyl-2-palmitoyl phosphatidylcholine (MPPC), the PEGylated derivates of the above phospholipids (such as PEG-distearyl phosphatidylethanolamine) or a mixture of them, preferably hydrogenated soybean phosphatidylcholine and PEG-distearyl phosphatidylethanolamine.

In the liquid composition of an insoluble medicament of this invention, the oil for injection are specifically selected from one of or a mixture of some of the following: soybean oil, corn oil, median chain triglyceride (MCT), castor oil, olive oil, peanut oil, cottonseed oil, sesame oil, safflower oil, glyceryl monostearate or glyceryl monooleate, and the like. Preferred is soybean oil, corn oil, median chain triglyceride or a mixture thereof. The oil for injection can further include long and medium chain fatty acids, long and medium chain fatty glyceride, long chain fatty alcohol, and a mixture of the above components, including saturated and unsaturated, straight and branched chain forms thereof.

In the liquid composition of an insoluble medicament of this invention, the solvent is selected from one of or a mixture of some of the following: absolute ethanol, glycerol, propylene glycol, PEG (polyethylene glycol), N,N-dimethyl acetamide, benzyl benzoate, ethyl oleate, benzyl alcohol and the like, wherein preferred is absolute ethanol, or a mixture of absolute ethanol and N,N-dimethyl acetamide, or a mixture of absolute ethanol and PEG, or a mixture of glycerol and N,N-dimethyl acetamide. Wherein, the PEG includes PEGs with different weight average molecular weights or a mixture thereof, and the weight average molecular weights range from 200 to 2000, preferably, 200-400. Wherein, the solid PEGs need to dissolve into other solvents firstly.

Pharmaceutically acceptable pharmaceutical additive(s), such as coemulsifier, stabilizing agent, pH regulator, antioxidant and the like, can be further added into the liquid composition of an insoluble medicament of this invention as required.

Wherein, the stabilizing agent can be one of or a combination of many of cholesterol, PEGs and the derivates thereof, glycerol, xylitol, sorbitol, mannitol, propylene glycol, glycerol, urea, sodium salicylate, phosphatidic acid, oleic acid, sodium oleate, cholic acid, sodium cholate, hypromellose, sodium carboxymethylcellulose, starch and the derivates thereof, poloxamer, gelatin and the derivates thereof, alginic acid and the salt thereof, polyvinyl pyrrolidone, hydroxypropyl-β-cyclodextrin.

The pH regulator can be one or more of maleic acid, hydrochloric acid, tartaric acid, sodium hydroxide, acetic acid, acetate, phosphoric acid, phosphate, citric acid, citrate, ethanolamine, triethanolamine, diethanolamine. Generally, the pH value range of the liquid composition is regulated to from 4 to 8.

The coemulsifier includes one of the derivatives of a variety of small molecule alcohols and polyglycerin, or a mixture thereof.

The antioxidant includes one or more of α-tocopherol, α-tocopherol succinate, ascorbyl palmitate, butylated hydroxyanisole (BHA), dibutyl phenol (BHT) or propyl gallate.

It should be appreciated that all the pharmaceutical additives well known to the skilled person in the art could be applied to the liquid composition of the invention, and the amount of the pharmaceutical additives is substantially the routine amount in the pharmacy field.

In addition, on the basis of this invention, a person skilled in the art knows how to make suitable modifications to the preferred ranges mentioned in this application according to the prior art and the different components to be used. These modifications do not depart from the spirit of this invention, and fall into the protection scope of claims of this invention.

The liquid composition of an insoluble medicament of this invention can be in injectable concentrated solution form, generally in injectable concentrated solution form with small volume, and can be sterilely filled into ampoules or small volume vials. The administration modes of the liquid composition are similar with the commercially available formulations such as TAXOL (paclitaxel injection), Taxotere (docetaxel injection), that is, being formulated with injectable solution before use, for injection. Preferably, the injectable concentrated solution is dispersed with 5% dextrose solution or normal saline or water for injection or a mixture thereof during clinical use, to form uniform hydration emulsion for injection, particularly for intravenous injection. The average particle size of the hydration emulsion ranges from 10 to 5000 nm.

Moreover, the liquid composition of an insoluble medicament of this invention can be formulated into capsule, soft capsule or oral liquid formulation based on the routine method of pharmacy, for oral use and the like.

As mentioned above, generally, the injections of insoluble medicaments, including ready-to-use injections, are difficult to prepare without Cremophor EL and Tween 80. This is because if the solubilization ability of the surfactant is not strong, the insoluble medicaments such as paclitaxel and the like tend to crystallize when formulated with aqueous medium such as water for injection. By a large amount of research, the invention has found that only when the insoluble medicaments, oil phase, phospholipid and organic solvent are in a very suitable ratio, can the prepared liquid composition be clear and transparent, and when hydrated with injectable solution, be stable within 8 hours without crystallization of medicaments, separation of layers, or flocculation, thus in conformity with the requirement for clinical medication. The reason for such a result may be that insoluble medicaments possess certain solubility in both organic solvent and oil phase, and the greatest solubility could be achieved at a suitable ratio, moreover the phospholipid possesses certain viscosity and stabilization by super-saturation, and could maintain the medicaments in oil phase, oil-water interface or form complicated phospholipid complex when emulsified with water. The above combined reasons render that the medicaments do not crystallize in a short time.

The amount of each component in the invention is very important. Only within the amount range of the invention, could the injections of insoluble medicaments, the stability of which meets the requirement, be prepared.

When the type of each component such as insoluble medicament, oil for injection, solvent or phospholipid changes, the amount thereof may be varied to a certain extent, but it is still in the amount range of the invention. However, when the amount of each component is beyond the amount range mentioned in the present invention, phenomena such as inability to form clear transparent solution, too high viscosity of the solution, or crystallization within 8 hours after hydration will occur, which is disadvantageous for clinical use. Parts of formula screening tests and the results can be seen in the Examples.

Similarly, the kind of each component in the invention is also very important, wherein the effects of phospholipid and organic solvent are indispensable, and wherein, for some extremely insoluble medicaments, it is required to simultaneously use N,N-dimethyl acetamide and absolute ethanol as organic solvents; whereas for some other insoluble medicaments such as docetaxel or paclitaxel, absolute ethanol alone or both N,N-dimethyl acetamide and absolute ethanol can be used as the organic solvent. Relatively, in terms of in vitro stability, the effect of oil phase is relatively low, and without the use of oil phase, injections could also be formulated, and could also maintain stable within 8 hours. Liposome could be formed when contacting water without adding oil phase, whereas the physiological dispositions of liposome and emulsion are different, and each has its own features, thus adding oil phase and not adding oil phase both fall into the protection scope of the invention.

Another aim of the invention is to provide a preparation method for the liquid composition of an insoluble medicament of this invention.

In one aspect, the preparation method of this invention includes: dissolving an insoluble medicament into solvent or oil for injection or a mixture thereof firstly, and then adding phospholipid and other components in the liquid composition, and mixing uniformly to form a transparent and clear liquid composition, i.e., the liquid composition of an insoluble medicament of this invention.

In another aspect, the preparation method of this invention includes: directly dissolving an insoluble medicament into a mixture of solvent, oil for injection, phospholipid and other components in the liquid composition, and mixing uniformly to form a transparent and clear liquid composition, i.e., the liquid composition of an insoluble medicament of this invention.

In yet another aspect, the preparation method of this invention includes: dissolving an insoluble medicament into part of solvent firstly, and then adding into a mixture of phospholipid, oil for injection, the remaining solvent and other components, and mixing uniformly to form a transparent and clear liquid, i.e., the liquid composition of an insoluble medicament of this invention.

The liquid composition of an insoluble medicament of this invention can be prepared into medicine products in a certain specification via a series of processes such as filtration, filling and the like.

The liquid composition of an insoluble medicament of this invention possesses the following advantages:

1. Using phospholipid, oil for injection such as soybean oil and the like with good biocompatibility instead of surfactants used in some currently commercially available injections of an insoluble medicament, such as polyoxyethylene castor oil (Cremophor EL) or polysorbate 80 (Tween 80), the hidden dangers such as severe hypersensitivity and haemolyticus of insoluble medicament formulation have been eliminated in the aspect of formula.

2. In the invention, dissolving an insoluble medicament into organic solvent or oil for injection or a mixture thereof could prevent oxidation, hydrolysis and the like of the insoluble medicament in the aqueous medium, improve the stability of the formulation, and prolong the shelf life. At the same time, due to the lack of water, the composition is a small volume concentrated solution, which is convenient for transport and storage.

3. The preparation process of the liquid composition is easy, convenient for industrial production.

4. The formulation method is nearly the same with that of the current formulation in clinical use, which will not increase the difficulty for use and be in favor of improving the compliance for medication.

5. After being hydrated with an injectable solution (such as 5% dextrose solution, normal saline, water for injection), this liquid composition is stable within 8 hours, which is in conformity with the requirement for clinical medication.

PREFERRED EMBODIMENTS OF THE INVENTION

The invention will be further illustrated and explained with reference to the Examples below, but the Examples below should not be construed as the limitation to the invention. The Examples included in this application are only to facilitate understanding the invention more completely. These Examples do not limit the scope mentioned and claimed herein in any way.

Example 1

Figure 1:
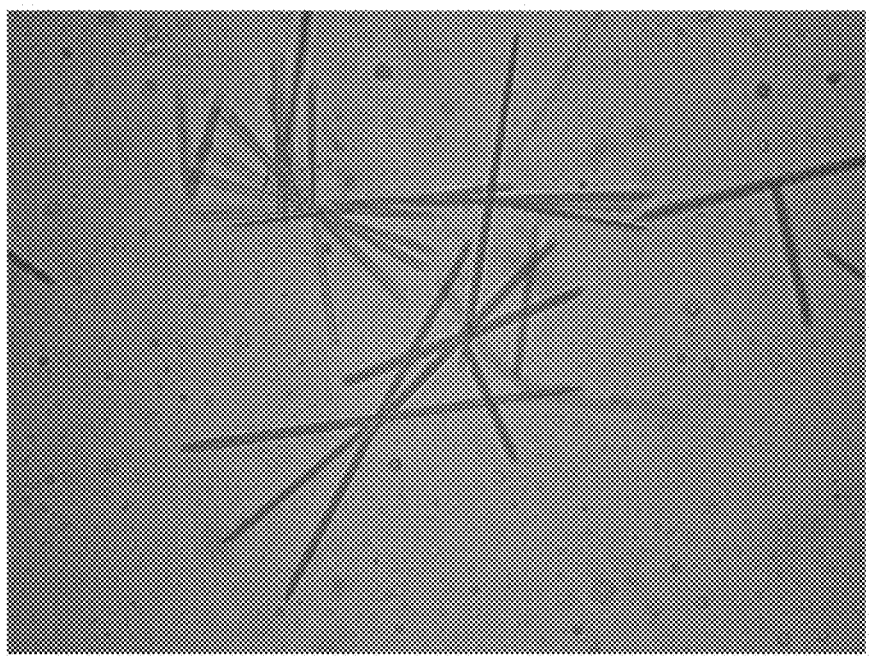
FIG. 1 shows the photograph of crystallization from hydration emulsion 8 hours after the liquid composition 3 in Example 1 was injected into 50 ml 5% dextrose injection.
Figure 2:
FIG. 2 shows the photograph of hydration emulsion 8 hours after the liquid composition 1 in Example 1 was injected into 50 ml 5% dextrose injection.

The Screening for the Liquid Composition of Paclitaxel 0.03 g paclitaxel (Guilin Huiang Biopharmaceutical Company, LTD) was weighed, added into 3 g absolute ethanol, stirred until the paclitaxel was completely dissolved, and then 1.2 g egg yolk lecithin (lecithinE80, LIPOID) and 0.12 g soybean oil (Zhejiang Tianyushan Medicinal Oil Development Co. LTD.) were added sequentially, and continued to stir to form liquid composition 1;

Liquid compositions 2-10 were prepared in the same method based on the composition of liquid compositions in Table 1 below. The liquid compositions 1-10 were observed for appearance, character and the solvency of each component; if the resulted liquid composition was transparent and clear, then it was injected into 50 ml 5% dextrose injection, oscillated slightly to form a uniform hydration emulsion, and left to stand for observation. After 8 hours, the appearance and character of the hydration emulsion were macroscopically observed. At the same time, the hydration emulsion was taken to observe the presence or absence of medicament crystallizing with microscope (Olympus XDS-1B inverted microscope, 40×). The composition of the liquid composition of paclitaxel and screening results can be seen in Table 1. The microphotographs for liquid composition 3 and liquid composition 1 can be seen in FIG. 1 and FIG. 2.

TABLE 1

The composition of the liquid composition of paclitaxel and screening results

| | paclitaxel | Lecithin E80 | soybean oil | organic solvent | character of liquid composition | observation after 8 hours |
|---|---|---|---|---|---|---|
| liquid composition 1 | 0.03 g | 1.2 g | 0.12 g | absolute ethanol 3 g | clear transparent | stable |

TABLE 1-continued

The composition of the liquid composition of paclitaxel and screening results

| | paclitaxel | Lecithin E80 | soybean oil | organic solvent | character of liquid composition | observation after 8 hours |
|---|---|---|---|---|---|---|
| liquid composition 2 | 0.03 g | 1.8 g | 0.12 g | absolute ethanol 3 g | clear transparent | stable |
| liquid composition 3 | 0.03 g | 0.3 g | 0.12 g | absolute ethanol 3 g | clear transparent | crystallized |
| liquid composition 4 | 0.03 g | 6 g | 0.4 g | absolute ethanol 5 g | clear transparent | stable |
| liquid composition 5 | 0.03 g | 2.4 g | 0.16 g | absolute ethanol 2.5 g | clear transparent | crystallized |
| liquid composition 6 | 0.03 g | 3.6 g | 0.24 g | absolute ethanol 2 g | poor flowability | N/A |
| liquid composition 7 | 0.03 g | 1.2 g | 0.12 g | absolute ethanol 1 g | clear transparent | stable |
| liquid composition 8 | 0.03 g | 1.2 g | 0.12 g | absolute ethanol 0.5 g | poor flowability | N/A |
| liquid composition 9 | 0.03 g | 1.2 g | 0.12 g | PEG400 1 g | phospholipid incompletely dissolved | N/A |
| liquid composition 10 | 0.03 g | 1.2 g | 0.12 g | glycerol 1 g | phospholipid incompletely dissolved | N/A | stable: There is no separation of layers, flocculation or medicament crystallizing for the hydration emulsion;
crystallized: Significant medicament crystallizing were observed with microscopy;
poor flowability: Liquid flows slowly, and is improper for sampling and loading;
phospholipid incompletely dissolved: Significant phospholipid agglomerate or floc can be seen;
N/A: not available.

The results show that, when the percentage by weight for each component of the liquid composition of paclitaxel is within the range of this invention, a clear and transparent solution is obtained, and keeps stable within 8 hours after being injected into 50 ml 5% dextrose injection for forming uniform hydration emulsion, without crystallizing. Whereas when the percentage by weight for each component of the liquid composition of paclitaxel is beyond the range of this invention, no clear and transparent solution is obtained, or even if a clear and transparent solution is obtained, within 8 hours after being injected into 50 ml 5% dextrose injection for forming uniform hydration emulsion, crystallization occurred. In addition, the average particle sizes of the hydration emulsions obtained from liquid compositions 1, 2, 4, and 7 were determined with a laser particle size analyzer (Zetasizer Nano ZS, Malvern, UK), and measured average particle sizes of the hydration emulsions were all within the range of 10-5000 nm, which is in conformity with the requirement for clinical medication.

Example 2

The Screening for the Liquid Composition of Docetaxel 1.6 g egg yolk lecithin (lecithin E80, LIPOID), 0.16 g soybean oil (Zhejiang Tianyushan Medicinal Oil Development Co. LTD.) were added into 4 g absolute ethanol firstly, stirred until uniform, then 0.08 g docetaxel (Guilin Huiang Biopharmaceutical Company, LTD) was added into the above mixture, continued to stir to form liquid composition 11.

Figure 3:
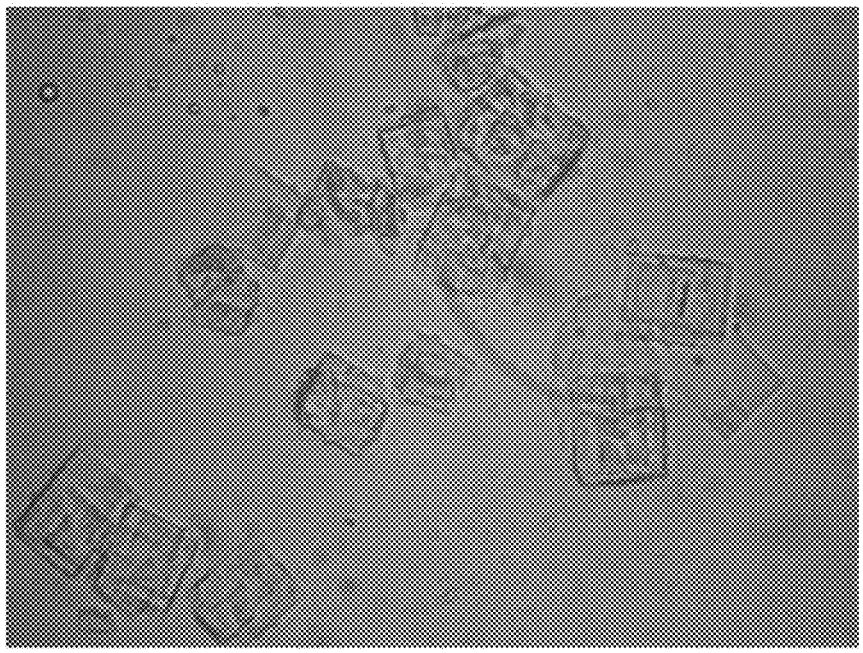
FIG. 3 shows the photograph of crystallization from hydration emulsion 8 hours after the liquid composition 15 in Example 2 was injected into 200 ml 5% dextrose injection.
Figure 4:
FIG. 4 shows the photograph of hydration emulsion 8 hours after the liquid composition 11 in Example 2 was injected into 200 ml 5% dextrose injection.

Liquid compositions 12-15 were prepared in the same method based on the composition of liquid compositions in Table 2 below. The liquid compositions 11-15 were observed for appearance, character and the solvency of each component; if the resulted liquid composition was transparent and clear, then it was injected into 200 ml 5% dextrose injection, oscillated slightly to form a uniform hydration emulsion, and left to stand for observation. After 8 hours, the appearance and character of the hydration emulsion were macroscopically observed. At the same time, the hydration emulsion was taken to observe the presence or absence of medicament crystallizing with microscope (Olympus XDS-1B inverted microscope, 40×). The composition of the liquid composition of docetaxel and screening results can be seen in Table 2. The microphotographs for liquid composition 15 and 11 can be seen in FIG. 3 and FIG. 4.

TABLE 2

The composition of the liquid composition of docetaxel and screening results

| | docetaxel | lecithin E80 | soybean oil | absolute ethanol | liquid composition character | observation after 8 hours |
|---|---|---|---|---|---|---|
| liquid composition 11 | 0.08 g | 1.6 g | 0.16 g | 4 g | clear transparent | stable |
| liquid composition 12 | 0.08 g | 0.8 g | 0.32 g | 4 g | clear transparent | stable |
| liquid composition 13 | 0.08 g | 0.8 g | 0.16 g | 3 g | clear transparent | stable |
| liquid composition 14 | 0.08 g | 4.8 g | 0.16 g | 4 g | clear transparent | stable |
| liquid composition 15 | 0.08 g | 0.2 g | 0.16 g | 1 g | clear transparent | crystallized | stable: There is no separation of layers, flocculation or medicament crystallizing for the hydration emulsion;
crystallized: Significant medicament crystallizing were observed with microscopy;

The results show that, when the percentage by weight for each component of the liquid composition of docetaxel is within the range of this invention, a clear and transparent solution is obtained, and keeps stable within 8 hours after being injected into 200 ml 5% dextrose injection for forming uniform hydration emulsion, without crystallizing. Whereas when the percentage by weight for each component of the liquid composition of docetaxel is beyond the range of this invention, even if a clear and transparent solution is obtained, within 8 hours after being injected into 200 ml 5% dextrose injection for forming uniform hydration emulsion, crystallization occurred. In addition, the average particle sizes of the hydration emulsions obtained from liquid compositions 11-14 were determined with a laser particle size analyzer (Zetasizer Nano ZS, Malvern, UK), and the measured average particle sizes of the hydration emulsions were all within the range of 10-5000 nm, which is in conformity with the requirement for clinical medication.

On this basis, the inventors of this invention further prepared other liquid compositions of paclitaxel, docetaxel of the invention, as well as liquid compositions of other insoluble medicaments, and observed the liquid property thereof and the stability within 8 hours after being injected into an injectable solution.

Example 3

Liquid Composition:

| | |
|---|---|
| paclitaxel | 0.03 g |
| soybean lecithin (lecithin S100) | 1.2 g |
| soybean oil | 0.12 g |
| absolute ethanol | 3 g |

Preparation Method:

0.03 g paclitaxel (Guilin Huiang Biopharmaceutical Company, LTD) was added into 1 g absolute ethanol, after completely dissolving, 1.2 g lecithin (S100, LIPOID), 0.12 g soybean oil and 2 g absolute ethanol were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation were macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 4

Liquid Composition:

| | |
|---|---|
| docetaxel | 0.08 g |
| egg yolk lecithin (lecithin E80) | 1.6 g |
| soybean oil | 0.16 g |
| absolute ethanol | 4 g |

Preparation Method:

0.08 g docetaxel (Guilin Huiang Biopharmaceutical Company, LTD) was added into 2 g absolute ethanol, after completely dissolving, 1.6 g lecithin E80 (LIPOID), 0.16 g soybean oil and 2 g absolute ethanol were added, and stirred until they were mixed uniformly to form a transparent and clear liquid composition. The liquid composition was injected into 400 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 5

Liquid Composition:

| | |
|---|---|
| Docetaxel | 0.08 g |
| egg yolk lecithin (lecithin E80) | 1.6 g |
| absolute ethanol | 4 g |

Preparation Method:

0.08 g docetaxel (Guilin Huiang Biopharmaceutical Company, LTD) was added into 2 g absolute ethanol, after completely dissolving, 1.6 g lecithin E80 (LIPOID), and 2 g absolute ethanol were added, and stirred until they were mixed uniformly to form a transparent and clear liquid composition. The liquid composition was injected into 200 ml 5% dextrose injection, oscillated slightly to form a uniform hydration emulsion, and left to stand for observation. After 8 hours, no separation of layers, flocculation were macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 6

Liquid Composition:

| | |
|---|---|
| Capecitabine | 0.5 g |
| egg yolk lecithin (lecithin E80) | 1.2 g |
| soybean oil | 0.12 g |
| absolute ethanol | 5 g |

Preparation Method:

0.5 g capecitabine (Tai zhou world Pharm & Chem Co. Ltd) was added into 1 g absolute ethanol, after completely dissolving, 1.2 g lecithin E80 (LIPOID), 0.12 g soybean oil and 2 g absolute ethanol were added, and stirred until they were mixed uniformly to form a transparent and clear liquid composition. The liquid composition was injected into 500 ml 5% dextrose injection, oscillated slightly to form a uniform hydration emulsion, and left to stand for observation. After 8 hours, no separation of layers, flocculation was macroscopically observed for the hydration emulsion, and no

Example 7

Liquid Composition:

| | |
|---|---|
| vinorelbine | 0.01 g |
| egg yolk lecithin (lecithin E80) | 1.2 g |
| soybean oil | 0.12 g |
| absolute ethanol | 3 g |

Preparation Method:

0.01 g vinorelbine (Wu han Yuancheng Technology) was added into 1 g absolute ethanol, after completely dissolving, 1.2 g lecithin E80 (LIPOID), 0.12 g soybean oil and 2 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 8

Liquid Composition:

| | |
|---|---|
| Temozolomide | 0.1 g |
| egg yolk lecithin (lecithin E80) | 1.2 g |
| soybean oil | 0.12 g |
| absolute ethanol | 3 g |

Preparation Method:

0.1 g temozolomide (Dalian Meilun Biology Technology Co., LTD) was added into 1 g absolute ethanol, after completely dissolving, 1.2 g lecithin E80 (LIPOID), 0.12 g soybean oil and 2 g absolute ethanol were added, and stirred until they were mixed uniformly to form a transparent and clear liquid composition. The liquid composition was injected into 200 ml normal saline, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 9

Liquid Composition:

| | |
|---|---|
| doxorubicin | 0.05 g |
| egg yolk lecithin (lecithin E80) | 2.4 g |
| soybean oil | 0.12 g |
| absolute ethanol | 3 g |

Preparation Method:

0.05 g doxorubicin (Zhejiang Hisun Pharmaceutical Co. Ltd) was added into 1 g absolute ethanol, after completely dissolving, 2.4 g lecithin E80 (LIPOID), 0.12 g soybean oil and 2 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 10

Liquid Composition:

| | |
|---|---|
| gefitinib | 0.25 g |
| egg yolk lecithin (lecithin E80) | 1.2 g |
| soybean oil | 0.12 g |
| absolute ethanol | 3 g |

Preparation Method:

0.25 g gefitinib (Dalian Meilun Biology Technology Co., LTD) was added into 1 g absolute ethanol, after completely dissolving, 1.2 g lecithin E80 (LIPOID), 0.12 g soybean oil and 2 g absolute ethanol were added, and stirred until they were mixed uniformly to form a transparent and clear liquid composition. The liquid composition was injected into 250 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 11

Liquid Composition:

| | |
|---|---|
| etoposide | 0.05 g |
| egg yolk lecithin (lecithin E80) | 3.0 g |
| soybean oil | 0.2 g |
| N,N-dimethyl acetamide | 0.3 g |
| absolute ethanol | 5 g |

Preparation Method:

0.05 g etoposide (Dalian Meilun Biology Technology Co., LTD) was added into 0.3 g N,N-dimethyl acetamide and 2 g absolute ethanol, after completely dissolving, 3 g lecithin E80 (LIPOID), 0.2 g soybean oil and 3 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 12

Liquid Composition:

| | |
|---|---|
| paclitaxel | 0.15 g |
| egg yolk lecithin (lecithin E80) | 6.0 g |
| soybean oil | 0.4 g |
| absolute ethanol | 10 g |

Preparation Method:

0.15 g paclitaxel (Guilin Huiang Biopharmaceutical Company, LTD) was added into 2 g absolute ethanol, after completely dissolving, 6 g lecithin E80 (LIPOID), 0.4 g soybean oil and 8 g absolute ethanol were added, and stirred until they were mixed uniformly to form a transparent and clear liquid composition. The liquid composition was injected into 250 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 13

Liquid Composition:

| | |
|---|---|
| Paclitaxel | 0.03 g |
| egg yolk lecithin (lecithin E80) | 1.2 g |
| soybean oil | 0.12 g |
| N,N-dimethyl acetamide | 0.06 g |
| absolute ethanol | 5 g |

Preparation Method:

0.03 g paclitaxel (Guilin Huiang Biopharmaceutical Company, LTD) was added into 0.06 g N,N-dimethyl acetamide and 2 g absolute ethanol, after completely dissolving, 1.2 g lecithin E80 (LIPOID), 0.12 g soybean oil and 3 g absolute ethanol were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 14

Liquid Composition:

| | |
|---|---|
| docetaxel | 0.08 g |
| egg yolk lecithin (lecithin E80) | 3.0 g |
| soybean oil | 1 g |
| absolute ethanol | 5 g |

Preparation Method:

0.08 g docetaxel (Guilin Huiang Biopharmaceutical Company, LTD) was added into 1 g soybean oil, after stirring uniformly, 3 g lecithin E80 (LIPOID) and 5 g absolute ethanol were added, and stirred until they were mixed uniformly to form a transparent and clear liquid composition. The liquid composition was injected into 200 ml 5% dextrose injection, oscillated slightly to form a uniform hydration emulsion, and left to stand for observation. After 8 hours, no separation of layers, flocculation was macroscopically observed for the hydration emulsion, and docetaxel medicament crystallizing was observed with a microscope (Olympus XDS-1B inverted microscope, 40×). The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 15

Liquid Composition:

| | |
|---|---|
| camptothecin | 0.05 g |
| hydrogenated soybean phosphatidylcholine | 3.0 g |
| soybean oil | 0.2 g |
| N,N-dimethyl acetamide | 0.3 g |
| absolute ethanol | 10 g |

Preparation Method:

0.05 g camptothecin (Chengdu Yuancheng Biotech Company, LTD) was added into 0.3 g N,N-dimethyl acetamide, after completely dissolving, 3 g hydrogenated soybean phosphatidylcholine HSPC (LIPOID), 0.2 g soybean oil and 10 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 16

Liquid Composition:

| | |
|---|---|
| paclitaxel | 0.03 g |
| egg yolk lecithin (lecithin E80) | 3.0 g |
| PEG-distearyl phosphatidylethanolamine | 0.4 g |
| soybean oil | 0.2 g |
| absolute ethanol | 5 g |

Preparation Method:

0.03 g paclitaxel (Guilin Huiang Biopharmaceutical Company, LTD) was added into 1 g absolute ethanol, after completely dissolving, 3 g lecithin E80 (LIPOID), 0.4 g PEG-distearylphosphatidylethanolamine (DSPE-PEG) (Japan NOF), 0.2 g soybean oil and 4 g absolute ethanol were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 17

Liquid Composition:

| | |
|---|---|
| paclitaxel | 0.03 g |
| egg yolk lecithin (lecithin E80) | 3.0 g |
| corn oil | 0.2 g |
| absolute ethanol | 5 g |

Preparation Method:

0.03 g paclitaxel (Guilin Huiang Biopharmaceutical Company, LTD) was added into 1 g absolute ethanol, after completely dissolving, 3 g lecithin E80 (LIPOID), 0.2 g corn oil and 4 g absolute ethanol were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 18

Liquid Composition:

| | |
|---|---|
| artemisinin | 0.05 g |
| egg yolk lecithin (lecithin E80) | 3.0 g |
| soybean oil | 0.2 g |
| N,N-dimethyl acetamide | 0.3 g |
| glycerol | 5 g |

Preparation Method:

0.05 g artemisinin (Hunan Huacheng Pharmaceutical Co., Ltd.) was added into 0.3 g N,N-dimethyl acetamide, after completely dissolving, 3 g lecithin E80 (LIPOID), 0.2 g soybean oil and 5 g glycerol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 19

Liquid Composition:

| | |
|---|---|
| paclitaxel | 0.03 g |
| egg yolk lecithin (lecithin E80) | 3.0 g |
| soybean oil | 0.2 g |
| absolute ethanol | 2.5 g |
| PEG400 | 2.5 g |

Preparation Method:

0.03 g paclitaxel (Guilin Huiang Biopharmaceutical Company, LTD) was added into the mixed solution of 1.25 g PEG400 and 1.25 g absolute ethanol, after completely dissolving, 3 g lecithin E80 (LIPOID), 0.2 g soybean oil, 1.25 g absolute ethanol and 1.25 g PEG400 were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 20

Liquid Composition:

| | |
|---|---|
| paclitaxel | 0.03 g |
| egg yolk lecithin (lecithin E80) | 3.0 g |
| soybean oil | 0.2 g |
| PEG400 | 5 g |
| maleic acid | q.s. |

Preparation Method:

0.03 g paclitaxel (Guilin Huiang Biopharmaceutical Company, LTD) was added into 1 g PEG400, after completely dissolving, 3 g lecithin E80 (LIPOID), 0.2 g soybean oil, and 4 g PEG400 were added, and stirred until they were mixed uniformly, then the pH value of the mixture was regulated with maleic acid to 4-8 to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 21

Liquid Composition:

| | |
|---|---|
| paclitaxel | 0.03 g |
| teniposide | 0.03 g |
| egg yolk lecithin (lecithin E80) | 3.0 g |
| soybean oil | 0.2 g |
| N,N-dimethyl acetamide | 0.3 g |
| absolute ethanol | 5 g |

Preparation Method:

0.03 g paclitaxel (Guilin Huiang Biopharmaceutical Company, LTD) and 0.03 g teniposide (Beijing Chemsynlab Pharmaceutical Science & Technology Co., Ltd) were added into the mixed solution of 1 g absolute ethanol and 0.3 g N,N-dimethyl acetamide respectively, after completely dissolving, 3 g lecithin E80 (LIPOID), 0.2 g soybean oil, and 4 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 22

Liquid Composition:

| | |
|---|---|
| teniposide | 0.05 g |
| egg yolk lecithin (lecithin E80) | 3.0 g |
| soybean oil | 0.2 g |
| N,N-dimethyl acetamide | 0.3 g |
| absolute ethanol | 5 g |

Figure 6:
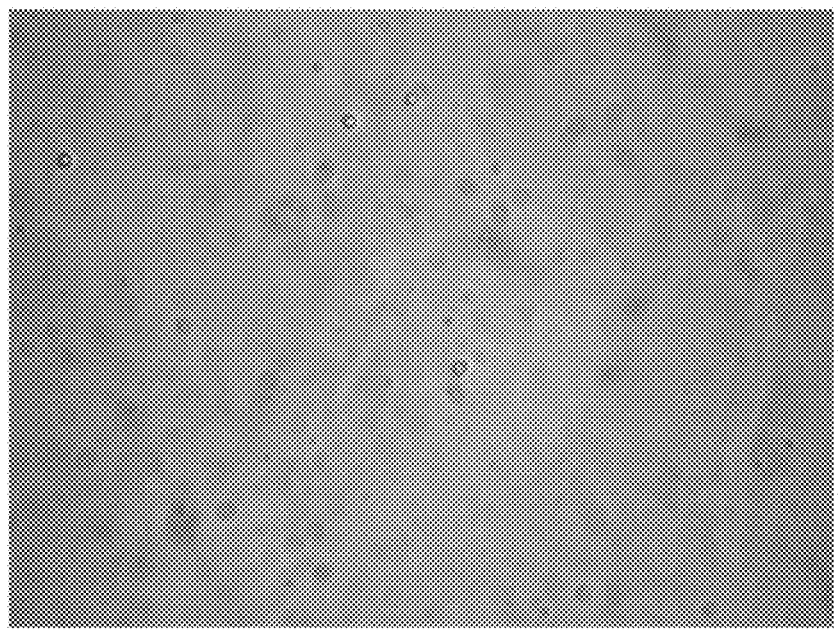
FIG. 6 shows the photograph of hydration emulsion 8 hours after the liquid composition in Example 22 was injected into 300 ml 5% dextrose injection.

Preparation Method:

0.03 g teniposide (Beijing Chemsynlab Pharmaceutical Science & Technology Co., Ltd) was added into the mixed solution of 1 g absolute ethanol and 0.3 g N,N-dimethyl acetamide, after completely dissolving, 3 g lecithin E80 (LIPOID), 0.2 g soybean oil, and 4 g absolute ethanol were added, and stirred until they were mixed uniformly to form a transparent and clear liquid composition. The liquid composition was injected into 300 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40×) for the hydration emulsion. Its microphotograph can be seen in FIG. 6. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 23

Liquid Composition:

| | |
|---|---|
| teniposide | 0.05 g |
| egg yolk lecithin (lecithin E80) | 1.2 g |
| soybean oil | 0.2 g |
| N,N-dimethyl acetamide | 0.3 g |
| absolute ethanol | 5 g |

Figure 5:
FIG. 5 shows the photograph of crystallization from hydration emulsion 8 hours after the liquid composition in Example 23 was injected into 300 ml 5% dextrose injection.

Preparation Method:

0.03 g teniposide (Beijing Chemsynlab Pharmaceutical Science & Technology Co., Ltd) was added into the mixed solution of 1 g absolute ethanol and 0.3 g N,N-dimethyl acetamide, after completely dissolving, 1.2 g lecithin E80 (LIPOID), 0.2 g soybean oil, and 4 g absolute ethanol were added, and stirred until they were mixed uniformly to form a transparent and clear liquid composition. The liquid composition was injected into 300 ml 5% dextrose injection, oscillated slightly to form a uniform hydration emulsion, and left to stand for observation. After 8 hours, no separation of layers, flocculation was macroscopically observed for the hydration emulsion, whereas medicament crystallizing was observed with a microscope (Olympus XDS-1B inverted microscope, 40x) for the hydration emulsion. Its microphotograph can be seen in FIG. 5.

Example 24

Liquid Composition:

| | |
|---|---|
| paclitaxel | 0.03 g |
| soybean lecithin (lecithin S100) | 1.2 g |
| soybean oil | 0.12 g |
| PEG200 | 1 g |
| absolute ethanol | 3 g |

Preparation Method:

0.03 g paclitaxel (Guilin Huiang Biopharmaceutical Company, LTD) was added into the mixed solution of 1 g absolute ethanol and 1 g PEG200, after completely dissolving, 1.2 g lecithin (S100, LIPOID), 0.12 g soybean oil, and 2 g absolute ethanol were added, and stirred until they were mixed uniformly to form a transparent and clear liquid composition. The liquid composition was injected into 50 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40x) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 25

Liquid Composition:

| | |
|---|---|
| paclitaxel | 0.03 g |
| soybean lecithin (lecithin S100) | 1.2 g |
| soybean oil | 0.12 g |
| PEG2000 | 1 g |
| absolute ethanol | 4 g |

Preparation Method:

0.03 g paclitaxel (Guilin Huiang Biopharmaceutical Company, LTD) was added into 2 g absolute ethanol, after completely dissolving, 1 g PEG2000, 1.2 g lecithin (S100, LIPOID), 0.12 g soybean oil, and 2 g absolute ethanol were added, and stirred until they were mixed uniformly to form a transparent and clear liquid composition. The liquid composition was injected into 100 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40x) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

Example 26

Liquid Composition:

| | |
|---|---|
| docetaxel | 0.08 g |
| egg yolk lecithin (lecithin E80) | 1.6 g |
| median chain triglyceride (MCT) | 0.2 g |
| absolute ethanol | 4 g |

Preparation Method:

0.08 g docetaxel (Guilin Huiang Biopharmaceutical Company, LTD) was added into 2 g absolute ethanol, after completely dissolving, 1.6 g lecithin E80 (LIPOID), 0.2 g median chain triglyceride (MCT, Tieling Beiya Oil Company, LTD), and 2 g absolute ethanol were added, and stirred until they were mixed uniformly to form a transparent and clear liquid composition. The liquid composition was injected into 200 ml 5% dextrose injection, oscillated slightly to form a uniform hydration emulsion, and left to stand for observation. After 8 hours, no separation of layers, flocculation was macroscopically observed for the hydration emulsion, and no medicament crystallizing was observed with a microscope (Olympus XDS-1B inverted microscope, 40x) for the hydration emulsion. The average particle size of the hydration emulsion was determined with a laser particle size analyzer (Zetasizer Nano ZS, Malvern, UK), and the measured average particle size of the hydration emulsion was within the range of 10-5000 nm, which is in conformity with the requirement for clinical medication.

When clinically used, the liquid composition of the invention was injected into 5% dextrose solutions or normal salines of different volumes for, after properly oscillating, administration by intravenous injection or drop infusion.

The results of the above Examples show that as long as the components of liquid composition of the invention and the amount of each component are within the ranges of the invention, a clear solution can be obtained, and after being hydrated with an injectable solution (such as 5% dextrose solution, normal saline, water for injection), the solution keeps stable within 8 hours, which is in conformity with the requirement for clinical medication.

Other aspects of the invention will be apparent to the skilled person in the art, and do not need to be repeated herein. The terms and wording used are illustrative but not for limitation, and use of these terms and wording is not intended to exclude any equivalent forms of technical features shown and described or fractions thereof. It should be appreciated that a variety of modifications can be within the scope of the invention.

INDUSTRIAL APPLICABILITY

The liquid composition of an insoluble medicament of this invention possesses the following advantages:

1. Using phospholipid, soybean oil and the like with good biocompatibility instead of surfactants used in some currently commercially available injections of an insoluble medicament, such as polyoxyethylene castor oil (Cremophor EL) or polysorbate 80 (Tween 80), the hidden dangers such as severe hypersensitivity and haemolyticus of insoluble medicament formulation have been eliminated in the aspect of formula.

2. In the invention, dissolving an insoluble medicament into organic solvent or oil for injection or a mixture thereof could prevent oxidation, hydrolysis and the like of the insoluble medicament in the aqueous medium, improve the stability of the formulation, and prolong the shelf life. At the same time, due to the lack of water, the composition is a small volume concentrated solution, which is convenient for transport and storage.

3. The preparation process of the liquid composition is easy, convenient for industrial production.

4. The formulation method is nearly the same with that of the current formulation in clinical use, which will not increase the difficulty for use and be in favor of improving the compliance for medication.

5. After being hydrated with an injectable solution (such as 5% dextrose solution, normal saline, water for injection), this liquid composition keeps stable within 8 hours, which is in conformity with the requirement for clinical medication.

What is claimed is:

1. A liquid composition of an insoluble medicament, said liquid composition containing insoluble medicament, oil for injection, phospholipid, and solvent, with the following percentage by weight for each component:
   insoluble medicament 0.01-10%,
   oil for injection 0%-20%,
   phospholipid 20-45%, and
   solvent 20-89%;
   wherein the liquid composition of an insoluble medicament does not contain surfactant of polyoxyethylene castor oil or polysorbate;
   wherein the liquid composition is a clear, transparent solution and does not contain water, and wherein the liquid composition is stable within 8 hours after being hydrated with injectable solvents.

2. The liquid composition of claim 1, wherein the percentage by weight for each component is as follows:
   insoluble medicament 0.1-2.5%,
   oil for injection 0.5%-10%,
   phospholipid 20-45%, and
   solvent 42.5-79%.

3. The liquid composition of claim 1, wherein the insoluble medicament is selected from: docetaxel, paclitaxel, capecitabine, oxaliplatin, gefitinib, doxorubicin, irinotecan, gemcitabine, pemetrexed, temozolomide, imatinib, vinorelbine, letrozole, teniposide, etoposide, podophyllotoxin, camptothecin, 10-hydroxycamptothecin, 9-hydroxycamptothecin, 7-ethyl-10-hydroxycamptothecin SN-38, topotecan, vinblastine, vincristine, vindesine, vinflunine, vinpocetine, norcantharidin, silibinin, propofol, florfenicol, mitiglinide, artemisinin, dihydroartemisinin, sirolimus, ibuprofen, nitrendipine, nicardipine, nimodipine, gliclazide, cisapride, nifedipine, felodipine, glibenclamide, acyclovir, oleanolic acid, breviscapine, ferulic acid, acetaminophen, clindamycin palmitate, penclomedine, Vitamin A, tamoxifen, navelbine, valproic acid, tacrolimus, ciclosporin A, amphotericin B, ketoconazole, domperidone, sulpiride, fenofibrate, bezafibrate, azithromycin, itraconazole, miconazole, brimoxidine, latanoprost, erythromycin, roxithromycin, rifaximin, cyclosporin, diclofenac, indomethacin, teldane, theophylline, ketoprofen, furosemide, spironolactone, dipyridamole, piroxicam, mefenamic acid, trichloromethiazide, indolol or a mixture thereof.

4. The liquid composition of claim 1, wherein the phospholipid is selected from natural phospholipids, semisynthetic phospholipids, synthetic phospholipids or a mixture thereof.

5. The liquid composition of claim 4, wherein said natural phospholipids are lecithin.

6. The liquid composition of claim 4, wherein said semisynthetic phospholipids and synthetic phospholipids are selected from hydrogenated soybean phosphatidylcholine (HSPC), dioleoyl phosphatidylcholine (DOPC), dimyristoyl phosphatidylethanolamine (DMPE), dipalmitoyl phosphatidylethanolamine (DPPE), dimyristoyl phosphatidylserine (DMPS), distearyl phosphatidylethanolamine (DSPE), dilauroyl phosphatidylcholine (DLPC), dimyristoyl phosphatidylcholine (DMPC), dipalmitoyl phosphatidylcholine (DPPC), distearyl phosphatidylcholine (DSPC), 1-myristoyl-2-palmitoyl phosphatidylcholine (MPPC), the PEGylated derivates of the above phospholipids or a mixture of them.

7. The liquid composition of claim 1, wherein said oil for injection is selected from one of or a mixture of some of soybean oil, corn oil, medium chain triglyceride (MCT), castor oil, olive oil, peanut oil, cottonseed oil, sesame oil, safflower oil, glyceryl monostearate or glyceryl monooleate.

8. The liquid composition of claim 1, wherein said solvent is selected from one of or a mixture of some of absolute ethanol, glycerol, propylene glycol, PEG, N,N-dimethyl acetamide, benzyl benzoate, ethyl oleate, or benzyl alcohol.

9. The liquid composition of claim 8, wherein said solvent is absolute ethanol or a mixture of absolute ethanol and N,N-dimethyl acetamide, or a mixture of absolute ethanol and PEG, or a mixture of glycerol and N,N-dimethyl acetamide.

10. The liquid composition of claim 1, further containing pharmaceutically acceptable pharmaceutical additive(s).

11. The liquid composition of claim 10, wherein said pharmaceutical additive(s) include coemulsifier, stabilizing agent, pH regulator and antioxidant.

12. The liquid composition of claim 1, wherein said liquid composition is in an injectable concentrated solution form, which is formulated with an injectable solution before use, for injection; or in a capsule, soft capsule or oral liquid formulation form.

13. The liquid composition of claim 12, wherein said injectable concentrated solution is dispersed with 5% dextrose solution or normal saline or water for injection or a mixture thereof during clinical use, to form a uniform hydration emulsion for intravenous injection.

14. The liquid composition of claim 2, wherein the insoluble medicament is selected from: docetaxel, paclitaxel, capecitabine, oxaliplatin, gefitinib, doxorubicin, irinotecan, gemcitabine, pemetrexed, temozolomide, imatinib, vinorelbine, letrozole, teniposide, etoposide, podophyllotoxin, camptothecin, 10-hydroxycamptothecin, 9-hydroxycamptothecin, 7-ethyl-10-hydroxycamptothecin SN-38, topotecan, vinblastine, vincristine, vindesine, vinflunine, vinpocetine, norcantharidin, silibinin, propofol, florfenicol, mitiglinide, artemisinin, dihydroartemisinin, sirolimus, ibuprofen, nitrendipine, nicardipine, nimodipine, gliclazide, cisapride, nifedipine, felodipine, glibenclamide, acyclovir, oleanolic acid, breviscapine, ferulic acid, acetaminophen, clindamycin palmitate, penclomedine, Vitamin A, tamoxifen, navelbine, valproic acid, tacrolimus, ciclosporin A, amphotericin B, ketoconazole, domperidone, sulpiride, fenofibrate, bezafibrate, azithromycin, itraconazole, miconazole, brimoxidine, latanoprost, erythromycin, roxithromycin, rifaximin, cyclosporin, diclofenac, indomethacin, teldane, theophylline, ketoprofen, furosemide, spironolactone, dipyridamole, piroxicam, mefenamic acid, trichloromethiazide, indolol or a mixture thereof.

15. The liquid composition of claim 2, wherein the phospholipid is selected from natural phospholipids, semisynthetic phospholipids, synthetic phospholipids or a mixture thereof.

16. The liquid composition of claim 2, wherein said oil for injection is selected from one of or a mixture of some of soybean oil, corn oil, medium chain triglyceride (MCT), castor oil, olive oil, peanut oil, cottonseed oil, sesame oil, safflower oil, glyceryl monostearate or glyceryl monooleate.

17. The liquid composition of claim 2, wherein said solvent is selected from one of or a mixture of some of absolute ethanol, glycerol, propylene glycol, PEG, N,N-dimethyl acetamide, benzyl benzoate, ethyl oleate, or benzyl alcohol.

18. The liquid composition of claim 2, further containing pharmaceutically acceptable pharmaceutical additive(s).

19. The liquid composition of claim 2, wherein said liquid composition is in an injectable concentrated solution form, which is formulated with an injectable solution before use, for injection; or in a capsule, soft capsule or oral liquid formulation form.

20. The liquid composition of claim 10, wherein said liquid composition is in an injectable concentrated solution form, which is formulated with an injectable solution before use, for injection; or in a capsule, soft capsule or oral liquid formulation form.

21. The liquid composition of claim 18, wherein said liquid composition is in an injectable concentrated solution form, which is formulated with an injectable solution before use, for injection; or in a capsule, soft capsule or oral liquid formulation form.

22. The liquid composition of claim 3, wherein the insoluble medicament is selected from: paclitaxel, docetaxel, capecitabine, vinorelbine, temozolomide, doxorubicin, gefitinib, teniposide, etoposide, podophyllotoxin, artemisinin, camptothecin, vinblastine or a mixture thereof.

23. The liquid composition of claim 22, wherein the insoluble medicament is selected from: paclitaxel, docetaxel, capecitabine, vinorelbine, temozolomide, doxorubicin, gefitinib, teniposide, etoposide, artemisinin, camptothecin or the mixture of paclitaxel and teniposide.

24. The liquid composition of claim 5, wherein said lecithin is selected from egg yolk lecithin, soybean lecithin or a mixture thereof in any proportion.

25. The liquid composition of claim 6, wherein said semisynthetic phospholipids and synthetic phospholipids are selected from hydrogenated soybean phosphatidylcholine and PEG-distearyl phosphatidylethanolamine.

26. The liquid composition of claim 7, wherein said oil for injection is selected from soybean oil, corn oil, medium chain triglyceride or a mixture thereof.

27. The liquid composition of claim 14, wherein the insoluble medicament is selected from: paclitaxel, docetaxel, capecitabine, vinorelbine, temozolomide, doxorubicin, gefitinib, teniposide, etoposide, podophyllotoxin, artemisinin, camptothecin, vinblastine or a mixture thereof.

28. The liquid composition of claim 27, wherein the insoluble medicament is selected from: paclitaxel, docetaxel, capecitabine, vinorelbine, temozolomide, doxorubicin, gefitinib, teniposide, etoposide, artemisinin, camptothecin or the mixture of paclitaxel and teniposide.

29. The liquid composition of claim 16, wherein said oil for injection is selected from soybean oil, corn oil, medium chain triglyceride or a mixture thereof.

30. A preparation method for the liquid composition of claim 1, characterized in that the insoluble medicament is dissolved into a solvent or an oil for injection or a mixture thereof, and then the phospholipid and other components in the liquid composition are added, and mixed uniformly to form the liquid composition; or the insoluble medicament is dissolved into a mixture of solvent, oil for injection, phospholipid and other components in the liquid composition, and mixed uniformly to form the liquid composition; or the insoluble medicament is dissolved into part of solvent firstly, and then added into a mixture of phospholipid, oil for injection, the remaining solvent and other components, and mixed uniformly to form the liquid composition.

\* \* \* \* \*